United States Patent
Suenaga et al.

(10) Patent No.: US 8,440,175 B2
(45) Date of Patent: May 14, 2013

(54) HAIR COSMETIC COMPOSITION

(75) Inventors: Koji Suenaga, Tokyo (JP); Masayuki Suzuki, Shizuoka (JP)

(73) Assignee: Momentive Performance Materials Japan LLC, Tokyo (JP)

( * ) Notice: Subject to any disclaimer, the term of this patent is extended or adjusted under 35 U.S.C. 154(b) by 581 days.

(21) Appl. No.: 12/221,454

(22) Filed: Jul. 31, 2008

(65) Prior Publication Data

US 2010/0028287 A1 Feb. 4, 2010

(51) Int. Cl.
*A61Q 5/02* (2006.01)
*A61Q 5/12* (2006.01)
*A01N 25/00* (2006.01)
*A61K 47/00* (2006.01)

(52) U.S. Cl.
USPC ..................... 424/70.122; 514/788

(58) Field of Classification Search ............... 424/70.122
See application file for complete search history.

(56) References Cited

FOREIGN PATENT DOCUMENTS

| JP | 03-264510 | 11/1991 |
|----|-----------|---------|
| JP | 08-217643 | 8/1996 |
| JP | 2005-132764 | 5/2005 |

OTHER PUBLICATIONS

Nasa, Toshihisa, Hair Cosmetic Composition, machine translation dated Oct. 30, 2010 of patent publication dated May 26, 2005, Japanese Patent Office, JP 2005132764 A.*

* cited by examiner

*Primary Examiner* — Gina C Justice
*Assistant Examiner* — Michael B Pallay
(74) *Attorney, Agent, or Firm* — Flynn, Thiel, Boutell & Tanis, P.C.

(57) ABSTRACT

A hair cosmetic composition which gives a feeling of light-sliding smoothness and a not-heavy feeling of not-unruliness to hair. The hair cosmetic composition contains a both terminally long-chain alkylamino group-modified polyorganosiloxane having a viscosity at 25° C. of 1,000 to 5,000,000 mPas, represented by the formula: $MD_xD'_yM$ wherein M is a siloxy unit represented by the formula: $R^1R^2{}_2SiO_{0.5}$, D is a siloxy unit represented by the formula: $R^2{}_2SiO$, and D' is a siloxy unit represented by the formula: $R^2R^3SiO$, where $R^1$ is an alkyl group having 12 to 50 carbon atoms, $R^2$ is a substituted or unsubstituted hydrocarbon group having 1 to 6 carbon atoms, $R^3$ is 3-aminopropyl group and/or N-(2-aminoethyl)-3-aminopropyl group, x is a value of 1 to 2,000, and y is a value of 1 to 50.

3 Claims, No Drawings

HAIR COSMETIC COMPOSITION

TECHNICAL FIELD

The present invention relates to a hair cosmetic composition, and especially relates to a hair cosmetic composition which gives feeling of light sliding smoothness and not-heavy feeling of not-unruliness to hair.

BACKGROUND ART

Conventionally, there have been proposed various types of hair cosmetic compositions where oil components such as a silicone oil (polyorganosiloxane), an ester oil and a hydrocarbon oil, cationic surfactants, or the like are blended to provide hair with feeling of smoothness (feeling of sliding smoothness), softness, moisture touch and the like. Particularly, the silicone oil can give an excellent gloss because of easiness of spreading uniformly to hairs due to low surface tension. Further, a silicone oil having widely varied viscosities can be used to give various feelings of touch. Therefore, hair cosmetics where silicone oil is used are widely disclosed in patent documents and the like.

JP-A 8-217643 discloses a formulation where an amino-modified silicone oil is blended. However, though the formulation is excellent in feeling of sliding smoothness, such a feeling is relatively heavy and does not satisfy the needs of recent consumers who require a light feeling of sliding smoothness.

Various silicone waxes are proposed for the purpose of providing both hair set processing property and light sliding smoothness (for example, JP-A 3-264510), but have not been used practically because the aimed effect is not enough due to its low adsorption to the hair and difficulty in remaining on the hair.

Moreover, the particular modified silicones having a combination of an amino group and an alkyl group are proposed (JP-A 2005-132764). However, though the effects of giving a sliding smoothness and moisture touch to hair are high, it cannot be said that they comply with recent consumers' needs as in the case of JP-A 8-217643.

DISCLOSURE OF THE INVENTION

The present invention has been made to solve those problems and provides a hair cosmetic composition which gives the feeling of a light sliding smoothness and a not-heavy feeling of not-unruliness to hair.

As a result of intensive study to accomplish the purpose, the present inventors have found that use of the particular both terminally long-chain alkylamino group-modified polyorganosiloxane is remarkably effective, and have completed the present invention.

Namely, the hair cosmetic composition of the present invention is characterized by containing a both terminally long-chain alkylamino group-modified polyorganosiloxane having a viscosity at 25° C. of 1,000 to 5,000,000 mPas, represented by the formula:

$$MD_xD'_yM$$

wherein M is a siloxy unit represented by the formula: $R^1R^2_2SiO_{0.5}$, D is a siloxy unit represented by the formula: $R^2_2SiO$, and D' is a siloxy unit represented by the formula: $R^2R^3SiO$, respectively, where $R^1$ is an alkyl group having 12 to 50 carbon atoms, $R^2$ is a substituted or un-substituted hydrocarbon group having 1 to 6 carbon atoms, $R^3$ is a 3-aminopropyl group and/or N-(2-aminoethyl)-3-aminopropyl group, x is a value of 1 to 2,000, and y is a value of 1 to 50.

According to the hair cosmetic composition of the present invention, it is preferable that the nitrogen content of the both terminally long-chain alkylamino group-modified polyorganosiloxane is 0.01 to 0.3% by weight. Further, the both terminally long-chain alkylamino group-modified polyorganosiloxane is preferably blended in the form of an emulsion to the hair cosmetic composition.

According to the hair cosmetic composition of the present invention, when used in hair-care products, the hair can be endowed with a feeling of light-sliding smoothness and not-heavy feeling of not-unruliness, which comply with recent consumers' needs.

DETAILED DESCRIPTION OF THE INVENTION

Embodiments of a hair cosmetic composition according to the present invention are described as follows. A hair cosmetic composition according to an embodiment of the present invention contains a polyorganosiloxane represented by the formula: $MD_xD'_yM$.

In the formula, M is a siloxy unit represented by the formula: $R^1R^2_2SiO_{0.5}$, D is a siloxy unit represented by the formula: $R^2_2SiO$, and D' is a siloxy unit represented by the formula: $R^2R^3SiO$, respectively.

Here, $R^1$ is an alkyl group having 12 to 50 carbon atoms, and may be linear or branched. Because of giving both a softness and light sliding smoothness to the hair at the same time as a hair cosmetic composition, among them, $R^1$ is preferably an alkyl group having 14 to 50 carbon atoms, and more preferably 16 to 50 carbon atoms.

$R^2$ is a substituted or un-substituted hydrocarbon group having 1 to 6 carbon atoms. Examples of the un-substituted hydrocarbon groups are, for instance, linear or branched alkyl groups such as methyl, ethyl, butyl or hexyl; cycloalkyl groups such as cyclohexyl; alkoxy groups such as methoxy, ethoxy, propoxy or butoxy; aryl groups such as phenyl, tryl or naphtyl; aralkyl groups such as benzyl, β-phenylethyl or methylbenzyl; alkenyl groups such as vinyl or allyl, and the like. Examples of the substituted alkyl groups are, for instance, fluoroalkyl groups such as 3,3,3-trifluoropropyl, and the like. Among them, preferable is an alkyl group or an aryl group, especially preferable is methyl or phenyl.

$R^3$ is 3-aminopropyl group and/or N-(2-aminoethyl)-3-aminopropyl group.

In the formula: $MD_x(D'_y)M$ which represents the both terminally long-chain alkylamino group-modified polyorganosiloxane used in the present invention, a value of x is within the range of 1 to 2,000, preferably within the range of 10 to 1,500. When the value of x is less than 1 and is more than 2,000, the resulting cosmetic compositions are inferior in smoothness (sliding smoothness) and, in each case, have an insufficient effect. A value of y is within the range of 1 to 50, particularly preferable within the range of 2 to 40. When the value of y is less than 1, the adsorption to hair is lower, and when more than 50, the feeling of sliding smoothness to dry hair becomes relatively heavy.

It is necessary that at 25° C., the viscosity of the both terminally long-chain alkylamino group-modified polyorganosiloxane of the present invention is 1,000 to 5,000,000 mPas, preferably 2,000 to 4,000,000 mPas. When the viscosity is less than 1,000 mPas, the feeling of sliding smoothness of the hair becomes relatively heavy, and when more than 5,000,000 mPas, the both terminally long-chain alkylamino group-modified polyorganosiloxane is hard to spread on the surface of hair uniformly. As a result, the feeling of sliding smoothness becomes also heavy in this case and thus the feeling of light sliding smoothness, which is the effect of the present invention, is hard to be obtained.

A nitrogen content of the both terminally long-chain alkylamino group-modified polyorganosiloxane is preferably 0.01 to 0.3% by weight because the feeling of light sliding smoothness can be provided, and is particularly preferably 0.05 to 0.25% by weight. When the nitrogen content is less than 0.01% by weight, the adsorption to hair is lower, and when more than 0.3% by weight, the feeling of sliding smoothness to dry hair becomes relatively heavy.

In the hair cosmetic composition of the present invention, when other silicone compounds are used at the same time, it is possible to meet the requirements to afford a more sensitive touch. When used together with other silicones, it is desirable to previously blend the silicones with each other, and then to use the blended product in the form of an emulsion.

Co-usable silicones include polydimethylsiloxane (dimethicone), cyclic polydimethylsiloxane (cyclomethicone), and the like. As the polydimethylsiloxane, at 25° C., those having a wide range of viscosity of 0.05 to 20,000 Pa·s can be used. Through blending, it is possible to adjust the smoothness particularly to dry hair. On the other hand, the cyclic polydimethylsiloxane can adjust the smoothness particularly to wet hair.

When the hair cosmetics are water types such as shampoos or rinses, it is preferable that the both terminally long-chain alkylamino group-modified polyorganosiloxane according to the present invention, or the blended product of the both terminally long-chain alkylamino group-modified polyorganosiloxane and the above-mentioned other silicones, is previously emulsified to be an emulsion, and then blended.

By being constituted in this way, the particle size of the silicone particles distributed in the hair cosmetics can be easily controlled, and adjustment of the feeling given becomes easy. Namely, an emulsion containing the silicone particles having a large particle size is suitable to a rinse and a conditioner which are cosmetics which are washed out after being applied, since the silicone portion easily remains on the hair. However, when the particle size is too large, there is a problem that the stability in the hair cosmetics becomes lowered. Therefore, the optimal particle size of the silicone particles is different depending on the type of respective hair cosmetics, and thus, it is necessary to control the particle size.

In the present invention, as a preparation method of the emulsion containing the both terminally long-chain alkylamino group-modified polyorganosiloxane, a publicly known method can be employed. For example, there are non-limiting emulsifying methods by using an emulsion machine such as a colloid mill, a line mixer, a homomixer, a homogenizer, or an integrated emulsion machine having an anchor mixer and homomixer, or an anchor mixer and disper mixer.

In the preparation of the emulsion, a surfactant and water are used. As the surfactant, any of an anionic surfactant, a cationic surfactant, a nonionic surfactant and an amphoteric surfactant may be used, and they may be used alone or as a mixture of two or more.

As the anionic surfactant, there are exemplified dodecylbenzenesulfonic acid, octylbenzenesulfonic acid, polyoxyethylene lauryl sulfate, lauryl sulfate, tetradecenesulfonic acid, hydroxytetradecenesulfonic acid, and sodium salt, potassium salt, triethanolamine salt thereof, and the like.

As the cationic surfactant, there are exemplified lauryltrimethylammonium hydroxide, stearyltrimethylammonium hydroxide, dioctyldimethylammonium hydroxide, distearyldimethylammonium hydroxide, lauryltrimethylammonium chloride, stearyltrimethylammonium chloride, cetyltrimethylammonium chloride, dicocyldimethylammonium chloride, distearyldimethylammonium chloride, benzalkonium chloride, stearyldimethylbenzylammonium chloride, and the like.

As the nonionic surfactant, there are exemplified polyoxyethylene lauryl ether, polyoxyethylene fatty acid ester, polyoxyethylene sorbitan fatty acid ester, sorbitan fatty acid ester, glycerine fatty acid ester, polyoxyethylene hardened castor oil, polyoxyethylene sorbitol fatty acid ester, and the like.

As the amphoteric surfactant, there are exemplified laurylamine oxide, lauryl betaine, cocamidopropyl betaine, and the like.

The type of surfactant is selected depending on compatibility with other components in the hair cosmetics. For example, when the target hair cosmetic composition is an anionic composition such as a shampoo, at least one surfactant selected from the anionic surfactant, the amphoteric surfactant and the nonionic surfactant is preferably used, and when the target hair cosmetic composition is a cationic composition such as a rinse, a conditioner or the like, at least one surfactant selected from the cationic surfactant, the amphoteric surfactant and the nonionic surfactant is preferably used. Particularly, the nonionic surfactant is preferably used, since the particle sizes of the emulsion can be controlled relatively easily, and blending with both the anionic composition and the cationic composition can be stably done.

Here, examples of the nonionic surfactants are polyoxyethylene (6) lauryl ether, polyoxyethylene (7) cetyl ether, polyoxyethylene (20) stearyl ether, polyoxyethylene (3) octylphenyl ether, polyoxyethylene (18) nonylphenyl ether, polyethylene glycol monostearate (EO14), polyethylene glycol distearate (EO80), polyoxyethylene (20) sorbitan, polyoxyethylene (20) hardened castor oil, polyoxyethylene (20) sorbitan monolaurate, polyoxyethylene (20) sorbitan monopalmitate, polyoxyethylene (6) sorbitan monostearate, polyoxyethylene (20) sorbitan trioleate, polyoxyethylene (40) sorbitan tetraoleate, polyoxyethylene (15) glyceryl monooleate, polyoxyethylene (15) glyceryl monostearate, sorbitan monopalmitate, polyoxyethylene (10) behenyl ether, polyoxyethylene (10) phytosterol, polyoxyethylene (10) polyoxypropylene (4) cetyl ether, polyoxyethylene (5) stearylamine, polyoxyethylene (8) stearylpropylenediamine, polyoxyethylene (5) cetyl ether sodium phosphate, and the like. Among those nonionic surfactants, one having a HLB value of 6 to 20 is preferably used together, since the stability of the resulting emulsion is good.

A blending amount of the surfactant is preferably within the range of 1 to 40% by weight of the whole emulsion, more preferably 2 to 20% by weight. When less than 1% by weight, it is difficult to disperse each component well, and when more than 40% by weight, the stability of the emulsion becomes lowered. A blending amount of water as a dispersing medium is preferably within the range of 20 to 90% by weight of the whole emulsion, more preferably 30 to 80% by weight.

At the time of emulsification, by neutralizing the amino portion with an acid, the stability of the emulsion can be improved. The acids used at that time include organic acids such as acetic acid or lactic acid, and inorganic acids such as hydrochloric acid, sulfuric acid or phosphoric acid.

Examples of the hair cosmetic composition according to the present invention include a shampoo, a rinse, a conditioner, a treatment, a hair styling product, a hair mousse, a hair cream, a gel, and the like. The individual cosmetics have different purposes but have the common characteristics of providing the hair with a smooth touch.

When the emulsion containing the both terminally long-chain alkylamino group-modified polyorganosiloxane according to the present invention is used as a rinse effective agent and a conditioner, it is desirable to blend one or more of the quaternary ammonium salts in an amount of 0.1 to 5% by weight to the whole hair cosmetic. When the quaternary ammonium salt is less than 0.1% by weight, the rinsing effect is not enough, and when more than 5% by weight, the viscosity of resulting hair cosmetics becomes so high that it is hard to use them.

Examples of the quaternary ammonium salts include cetyltrimethylammonium chloride, stearyltrimethylammonium chloride, behenyltrimethylammonium chloride, behenyldimethylhydroxycetylammonium chloride, stearyldimethylammonium chloride, cetyltriethylammonium methyl sulfate, and the like. Among them, stearyltrimethylammonium chloride, behenyltrimethylammonium chloride and stearyldimethylbenzylammonium chloride are particularly preferable.

When using the emulsion containing the both terminally long-chain alkylamino group-modified polyorganosiloxane of the present invention as a detergent such as a shampoo, anionic surfactants such as a fatty acid soap, α-acylsulfonate, alkylsulfonate, alkylnaphthalenesulfonate, alkylsulfate, polyoxyethylene alkyl ether sulfate, alkylamide sulfate, alkylphosphate, alkylamidephosphate, alkyloyl alkyl taurate or N-acylamino acid salt; nonionic surfactants, for example, glycerine fatty acid esters such as glyceryl monostearate and glyceryl monooleate, sorbitan fatty acid esters such as sorbitan stearate or sorbitan oleate, polyoxyethylene sorbitan fatty acid esters such as polyoxyethylene sorbitan palm oil fatty acid ester, polyoxyethylene sorbitan monopalmitate or plyoxyethylene sorbitane monostearate, polyoxyethylene alkyl ethers such as polyoxyethylene laurylether or polyoxyethylene stearyl ether, polyethylene glycol fatty acid esters such as polyethylene glycol monolaurate, polyethylene glycol distearate or glycol distearate, and alkylalkanol amides such as lauric acid diethanolamide or palm oil fatty acid diethanolamide; and anphoteric surfactants, for example, betaines such as lauryl dimethylaminoacetic acid betaine, stearyl dimethylaminoacetic acid betaine, 2-alkyl-N-carboxymethyl-N-hydroxyethylimidazolinium betaine, palm oil fatty acid amidopropyl betaine or lauric acid amidopropyl betaine, aminocarboxylate, and imidazoline derivative. It is desirable that one or more of the surfactants are added to the hair cosmetic composition in an amount of 5 to 40% by weight. When less than 5%, by weight is added, the detergency and foaming property are lowered, and when more than 40% by weight is added, the viscosity of the resulting hair cosmetics becomes so high that it is hard to use them.

In the hair cosmetic composition of the present invention, other than the aforementioned components, there may be blended, depending on the intended use, oil components such as liquid paraffin, squalane, lanolin derivative, higher alcohol or various ester oils, water-soluble oil components such as ethylene glycol, propylene glycol, glycerin or sorbitol polyethylene glycol, moisturizers such as hyaluronic acid, chondroitin acid or pyrrolidone carboxylic acid, thickeners such as carboxyvinyl polymers, cationic polymers such as cation-modified cellulose ether derivatives, polyvinylpyrrolidone derivative quaternary ammonium salts, diaryl dimethylammonium chlorides, polyamide derivative quaternary ammonium salts, polyoxyethylenes, poyalkylenes or polyamines, ultraviolet ray absorbents, perfumes, and the like.

EXAMPLES

Examples and comparative examples are described as follows. In those examples, "parts" and "%," are "parts by weight" and "% by weight", respectively.

Example 1

42 parts of an alkyl-modified polyorganosiloxane represented by the formula: $M^A D_{25} M^A$, 696 parts of octamethylcyclotetrasiloxane, and 12 parts of N-(2-aminoethyl)-3-aminopropylmethyldimethoxysilane were heated to 90° C. with stirring. Then, after adding 90 ppm of the effective ingredient in a 27% aqueous solution of tetramethylammonium hydroxide, an equilibration reaction was carried out at 90° C. for 3 hours to obtain a both terminally long-chain alkylamino group-modified polyorganosiloxane A having a nitrogen content of 0.22% and a viscosity of 2,240,000 mPas.

Besides, $M^A$ is the siloxy unit represented by the chemical formula: $R^A (CH_3)_2 SiO_{0.5}$, and $R^A$ is an alkyl group having the distribution of 30 to 45 carbon atoms.

Next, to 100 parts of the obtained both terminally long-chain alkylamino group-modified polyorganosiloxane A were added 10 parts of polyoxyethylene (4) lauryl ether and 24 parts of polyoxyethylene (6) lauryl ether, 14 parts of polyoxyethylene (23) lauryl ether, and stirred at 70° C. By adding 40 parts of ion-exchanged water gradually thereto, stirring was carried out at 70° C. Further, after adding 0.6 part of acetic acid and stirring, the stirring was continued by adding 211 parts of ion-exchanged water gradually to obtain a silicone emulsion (E-1).

A shampoo composition was prepared by using the thus obtained silicone emulsion (E-1) according to the formulation shown in Table 1.

Example 2

The same procedures as in Example 1 were repeated except that 35 parts of alkyl-modified polyorganosiloxane represented by the formula: $M^B D_{20} M^B$, 704 parts of octamethylcyclotetrasiloxane, and 11 parts of N-(2-aminoethyl)-3-aminopropylmethyldimethoxysilane were used to obtain a both terminally long-chain alkylamino group-modified polyorganosiloxane polyorganosiloxane B having a nitrogen content of 0.20% and a viscosity of 10,000 mPas. Besides, $M^B$ is the siloxy unit represented by the chemical formula: $R^B(CH_3)_2 SiO_{0.5}$, and $R^B$ is an alkyl group having the distribution of 20 to 28 carbon atoms.

Next, a silicone emulsion (E-2) was prepared by using the obtained both terminally long-chain alkylamino group-modified polyorganosiloxane B in the same manner as in Example 1.

A shampoo composition was prepared by using the thus obtained silicone emulsion (E-2) according to the formulation shown in Table 1.

Example 3

The same procedures as in Example 1 were repeated except that 32 parts of an alkyl-modified polyorganosiloxane represented by the formula: $M^C D_{20} M^C$, 706 parts of octamethylcyclotetrasiloxane, and 12 parts of N-(2-aminoethyl)-3-aminopropylmethyldimethoxysilane were used to obtain a both terminally long-chain alkylamino group-modified polyorganosiloxane C having a nitrogen content of 0.22% and a viscosity of 19,000 mPas. Besides, $M^C$ is the siloxy unit represented by the chemical formula: $R^C(CH_3)_2 SiO_{0.5}$, and $R^C$ is an alkyl group having 18 carbon atoms.

Next, a silicone emulsion (E-3) was prepared by using the obtained both terminally long-chain alkylamino group-modified polyorganosiloxane C in the same manner as in Example 1.

A shampoo composition was prepared by using the thus obtained silicone emulsion (E-3) according to the formulation shown in Table 1.

Example 4

The same procedures as in Example 1 were repeated except that 14 parts of an alkyl-modified polyorganosiloxane represented by the aforementioned formula: $M^C D_{20} M^C$, 733 parts of octamethylcyclotetrasiloxane, and 3 parts of N-(2-aminoethyl)-3-aminopropylmethyldimethoxysilane were used to obtain a both terminally long-chain alkylamino group-modified polyorganosiloxane D having a nitrogen content of 0.05% and a viscosity of 100,000 mPas.

Next, a silicone emulsion (E-4) was prepared by using the obtained both terminally long-chain alkylamino group-modified polyorganosiloxane D in the same manner as in Example 1.

A shampoo composition was prepared by using the thus obtained silicone emulsion (E-4) according to the formulation shown in Table 1.

Comparative Example 1

To 100 parts of the alkyl-modified polyorganosiloxane (wax like, melting point 70° C.) represented by the formula: $M^A D_{25} M^A$ were added 10 parts of polyoxyethylene (4) lauryl ether and 24 parts of polyoxyethylene (6) lauryl ether, 14 parts of polyoxyethylene (23) lauryl ether, and stirred at 80° C. By adding 40 parts of ion-exchanged water gradually thereto, stirring was carried out at 80° C. Further stirring was continued by adding 211 parts of ion-exchanged water gradually with an agihomomixer to obtain a silicone emulsion (E-5).

A shampoo composition was prepared by using the thus obtained silicone emulsion (E-5) according to the formulation shown in Table 1.

Comparative Example 2

50 parts of an alkyl-modified polyorganosiloxane represented by the formula: $MD^D{}_{50}M$, and 50 parts of an amino-modified polyorganosiloxane represented by the formula: $MD_{320}D'_8M$ were heated to 140° C. with stirring. Then, after adding 20 ppm of potassium hydroxide, an equilibration reaction was carried out at 140° C. for 5 hours to obtain an alkylamino-modified polyorganosiloxane E having a nitrogen content of 0.44% and a viscosity of 1,500 mPa·s. Besides, M is the siloxy unit represented by the chemical formula: $(CH_3)_3SiO_{0.5}$, $D^D$ is the siloxy unit represented by the chemical formula: $R^D(CH_3)SiO$, and D' is the siloxy unit represented by $(CH_3)[H_2N(CH_2)_2NH(CH_2)_3]SiO$, respectively. $R^C$ is an alkyl group having 14 carbon atoms.

Next, a silicone emulsion (E-6) was prepared by using the alkylamino-modified polyorganosiloxane E in the same manner as in Example 1.

A shampoo composition was prepared by using the thus obtained silicone emulsion (E-6) according to the formulation shown in Table 1.

Comparative Example 3

The same procedures as in Example 1 were repeated except that the amino-modified polyorganosiloxane represented by the formula: $MD_{1500}D'_4M$ (nitrogen content 0.10%, viscosity 100,000 mPa·s) was used to obtain a silicone emulsion (E-7). Besides, M is the siloxy unit represented by the chemical formula: $(CH_3)_3SiO_{0.5}$.

A shampoo composition was prepared by using the thus obtained silicone emulsion (E-7) according to the formulation shown in Table 1.

Comparative Example 4

The same procedures as in Example 1 were repeated except that 75 parts of an alkyl-modified polyorganosiloxane represented by the aforementioned formula: $M^C D_{20} M^C$, 622 parts of octamethylcyclotetrasiloxane, and 53 parts of N-(2-aminoethyl)-3-aminopropylmethyldimethoxysilane were used to obtain a both terminally long-chain alkylamino group-modified polyorganosiloxane F having a nitrogen content of 0.96% and a viscosity of 2,100 mPas.

Next, a silicone emulsion (E-8) was prepared by using the both terminally long-chain alkylamino group-modified polyorganosiloxane F in the same manner as in Example 1.

A shampoo composition was prepared by using the thus obtained silicone emulsion (E-8) according to the formulation shown in Table 1.

Next, the properties of the shampoo compositions prepared by the aforementioned Examples 1 to 4 and Comparative Examples 1 to 4 were evaluated, respectively, according to the following methods and standards.

(Evaluation Method)

Twelve panelists dipped 10 g of 25 cm long hair in water of 40° C., washed with 2 g of the shampoo composition for one minute, rinsed with water of 40° C. for 30 seconds, and dried with a dryer to prepare hair samples. In the hair sample preparation process, the individual panelists judged and rated "Feeling of fingers combing when washing hair", "Feeling of fingers combing when rinsing hair", "sliding smoothness after drying" and "softness after drying" according to the following 5-grade evaluation to calculate an average score.

| (Evaluation Standard) | |
|---|---|
| 5 | Extremely excellent |
| 4 | Excellent |
| 3 | Good |
| 2 | Slightly inferior |
| 1 | Inferior |

The results are shown in Table 1.

Examples 5 to 8, Comparative Examples 5 to 8

Hair Conditioner Composition

Conditioner compositions were prepared by using the silicone emulsions (E-1) to (E-8) used in the aforementioned Examples 1 to 4 and Comparative Examples 1 to 4 according to the formulation shown in Table 2, respectively.

Next, the properties of those conditioner compositions were evaluated according to the following methods and standards.

(Evaluation Method)

Twelve panelists dipped 10 g of 25 cm long hair in water of 40° C., applied 2 g of the conditioner composition onto the wetted hair, after one minute, rinsed with water of 40° C. for 30 seconds, and dried with a dryer to prepare hair samples. In the hair sample preparation process, the individual panelists judged and rated "Feeling of fingers combing when washing hair", "Feeling of fingers combing when rinsing hair", "sliding smoothness after drying" and "softness after drying" according to the following 5-grade evaluation to calculate an average score.

| (Evaluation Standard) | |
|---|---|
| 5 | Extremely excellent |
| 4 | Excellent |
| 3 | Good |
| 2 | Slightly inferior |
| 1 | Inferior |

The results are shown in Table 2.

TABLE 1

Shampoo

| Formulation part by weight | Example 1 | Example 2 | Example 3 | Example 4 | Comparative Example 1 | Comparative Example 2 | Comparative Example 3 | Comparative Example 4 |
|---|---|---|---|---|---|---|---|---|
| Silicone emulsion E-1 | 4 | | | | | | | |
| Silicone emulsion E-2 | | 4 | | | | | | |
| Silicone emulsion E-3 | | | 4 | | | | | |
| Silicone emulsion E-4 | | | | 4 | | | | |
| Silicone emulsion E-5 | | | | | 4 | | | |
| Silicone emulsion E-6 | | | | | | 4 | | |
| Silicone emulsion E-7 | | | | | | | 4 | |
| Silicone emulsion E-8 | | | | | | | | 4 |
| Polyoxyethylene (2) lauryl ether sodium sulfate (27% aqueous solution) | 33 | 33 | 33 | 33 | 33 | 33 | 33 | 33 |
| Cocamidopropyl betaine (30% aqueous solution) | 15 | 15 | 15 | 15 | 15 | 15 | 15 | 15 |
| Cokamido MEA | 1.5 | 1.5 | 1.5 | 1.5 | 1.5 | 1.5 | 1.5 | 1.5 |
| Ethylene glycol distearate | 2 | 2 | 2 | 2 | 2 | 2 | 2 | 2 |
| Glycerin | 3 | 3 | 3 | 3 | 3 | 3 | 3 | 3 |
| Polyquatanium-10 | 0.5 | 0.5 | 0.5 | 0.5 | 0.5 | 0.5 | 0.5 | 0.5 |
| Sodium benzoate | 0.15 | 0.15 | 0.15 | 0.15 | 0.15 | 0.15 | 0.15 | 0.15 |
| Perfume | 0.2 | 0.2 | 0.2 | 0.2 | 0.2 | 0.2 | 0.2 | 0.2 |
| Purified water | 40.65 | 40.65 | 40.65 | 40.65 | 40.65 | 40.65 | 40.65 | 40.65 |
| (Evaluated properties) | | | | | | | | |
| Feeling of fingers combing when washing hair | 4.1 | 4.1 | 4.4 | 4.2 | 1.9 | 3.5 | 3.3 | 3.9 |
| Feeling of fingers combing when rinsing hair | 4.0 | 4.1 | 4.2 | 4.1 | 2.2 | 3.2 | 3.4 | 3.8 |
| Sliding smoothness after drying | 4.0 | 4.2 | 4.3 | 4.3 | 2.3 | 3.5 | 3.9 | 3.1 |
| Softness after drying | 4.5 | 4.0 | 4.3 | 4.2 | 2.5 | 3.1 | 3.8 | 3.3 |

TABLE 2

Conditioner

| Formulation part by weight | Example 5 | Example 6 | Example 7 | Example 8 | Comparative Example 5 | Comparative Example 6 | Comparative Example 7 | Comparative Example 8 |
|---|---|---|---|---|---|---|---|---|
| Silicone emulsion E-1 | 8 | | | | | | | |
| Silicone emulsion E-2 | | 8 | | | | | | |
| Silicone emulsion E-3 | | | 8 | | | | | |
| Silicone emulsion E-4 | | | | 8 | | | | |
| Silicone emulsion E-5 | | | | | 8 | | | |
| Silicone emulsion E-6 | | | | | | 8 | | |
| Silicone emulsion E-7 | | | | | | | 8 | 8 |
| Ethylene glycol distearate | 3 | 3 | 3 | 3 | 3 | 3 | 3 | 3 |
| Cetanol | 2 | 2 | 2 | 2 | 2 | 2 | 2 | 2 |
| Propylene glycol monostearate | 3 | 3 | 3 | 3 | 3 | 3 | 3 | 3 |
| Glycerin monostearate | 3.8 | 3.8 | 3.8 | 3.8 | 3.8 | 3.8 | 3.8 | 3.8 |
| Polyoxyethylene (3) stearate | 3.8 | 3.8 | 3.8 | 3.8 | 3.8 | 3.8 | 3.8 | 3.8 |
| Cetyltrimethylammonium chloride | 5 | 5 | 5 | 5 | 5 | 5 | 5 | 5 |
| Polyoxyethylene (20) cetyl ether | 2 | 2 | 2 | 2 | 2 | 2 | 2 | 2 |
| 1,3-Butylene glycol | 5 | 5 | 5 | 5 | 5 | 5 | 5 | 5 |
| Paraben | 0.2 | 0.2 | 0.2 | 0.2 | 0.2 | 0.2 | 0.2 | 0.2 |
| Perfume | 0.2 | 0.2 | 0.2 | 0.2 | 0.2 | 0.2 | 0.2 | 0.2 |
| Purified water | 64 | 64 | 64 | 64 | 64 | 64 | 64 | 64 |
| (Evaluated properties) | | | | | | | | |
| Feeling of fingers combing when washing hair | 4.4 | 4.1 | 4.3 | 4.0 | 2.2 | 4.1 | 4.2 | 4.0 |
| Feeling of fingers combing when rinsing hair | 4.3 | 4.2 | 4.2 | 4.1 | 2.5 | 3.9 | 3.6 | 3.5 |
| Sliding smoothness after drying | 4.3 | 4.5 | 4.7 | 4.4 | 2.7 | 4.0 | 4.2 | 3.2 |
| Softness after drying | 4.7 | 4.2 | 4.4 | 4.2 | 1.9 | 3.2 | 3.5 | 3.3 |

The invention claimed is:

1. A hair cosmetic composition comprising a both terminally long-chain alkylamino group-modified polyorganosiloxane having a viscosity at 25° C. of 1,000-5,000,000 mPas, represented by the formula:

$$MD_xD'_yM$$

wherein M is a siloxy unit represented by the formula: $R^1R^2{}_2SiO_{0.5}$, D is a siloxy unit represented by the formula: $R^2{}_2SiO$, and D' is a siloxy unit represented by the formula: $R^2R^3SiO$, where $R^1$ is an alkyl group having 12-50 carbon atoms, $R^2$ is methyl, $R^3$ is either a 3-aminopropyl group or an N-(2-aminoethyl)-3-aminopropyl group, x is a value of 1-2,000 and y is a value of 1-50.

2. The hair cosmetic composition of claim 1, wherein the nitrogen content of the both terminally long-chain alkylamino group-modified polyorganosiloxane is 0.01 to 0.3% by weight, based on the weight of the polyorganosiloxane.

3. The hair cosmetic composition of claim 1, wherein the both terminally long-chain alkylamino group-modified polyorganosiloxane is blended in the hair cosmetic composition, which is in the form of an emulsion.

* * * * *